US009639658B2

(12) United States Patent
Vockley et al.

(10) Patent No.: US 9,639,658 B2
(45) Date of Patent: May 2, 2017

(54) ANCESTRAL-SPECIFIC REFERENCE GENOMES AND USES IN DETERMINING PROGNOSIS

(71) Applicant: Inova Health System, Falls Church, VA (US)

(72) Inventors: Joseph Vockley, Damascus, MD (US); John Niederhuber, Potomac, MD (US)

(73) Assignee: INOVA HEALTH SYSTEM, Falls Church, VA (US)

( * ) Notice: Subject to any disclaimer, the term of this patent is extended or adjusted under 35 U.S.C. 154(b) by 0 days.

(21) Appl. No.: 15/249,397

(22) Filed: Aug. 27, 2016

(65) Prior Publication Data
US 2017/0017753 A1 Jan. 19, 2017

Related U.S. Application Data

(62) Division of application No. 13/834,685, filed on Mar. 15, 2013, now Pat. No. 9,449,143.

(60) Provisional application No. 61/694,155, filed on Aug. 28, 2012.

(51) Int. Cl.
| G01N 33/48 | (2006.01) |
| G06F 19/18 | (2011.01) |
| C40B 30/02 | (2006.01) |
| G06F 19/14 | (2011.01) |
| G06F 19/22 | (2011.01) |

(52) U.S. Cl.
CPC .............. *G06F 19/18* (2013.01); *C40B 30/02* (2013.01); *G06F 19/14* (2013.01); *G06F 19/22* (2013.01)

(58) Field of Classification Search
CPC ...................................................... G06F 19/18
USPC ........................................................... 702/19
See application file for complete search history.

(56) References Cited

U.S. PATENT DOCUMENTS

| 8,306,942 B2 | 11/2012 | Chen et al. |
| 8,315,818 B2 | 11/2012 | Lois et al. |
| 2009/0239223 A1 | 9/2009 | Gehrmann et al. |
| 2010/0145893 A1 | 6/2010 | Semizarov et al. |

OTHER PUBLICATIONS

Complete Genomics Homepage, Retrieved from the Internet at http://www.completegenomics.com/, retrieved on Jan. 14, 2014.
Illumina Homepage, retrieved from the Internet at http://www.illumina.com/, retrieved on Jan. 14, 2014.
Illumina Services, retrieved from the Internet at http://www.illumina.com/services.ilmn/, retrieved on Jan. 14, 2014.
International Hap Map Project, retrieved from the Internet at http://www.hapmap.ncbi.nlm.nih.gov/, retrieved on Jan. 14, 2014.
Landes Bioscience Madame Curie Database, Chapter Details, "Pharmacogenetics, Ethnic Differences in Drug Response and Drug Regulation," retrieved from the Internet at http://www.landesbioscience.com/curie/chapter/3119/, Aug. 2007, retrieved on Jan. 14, 2014.
National Center for Biotechnology Information (NCBI) Homepage, retrieved from the Internet at http://www.ncbi.nlm.nih.gov/, retrieved on Jan. 14, 2014.
Online Mendelian Inheritance in Man (OMIM), retrieved from the Internet at http://www.ncbi.nlm.nih.gov/omim, retrieved on Jan. 14, 2014.
Pacific Biosciences Homepage, retrieved from the Internet at http://www.pacificbiosciences.com, retrieved on Jan. 14, 2014.
Institute for Systems Biology Family Genomics Group—Publications, retrieved from the Internet at http://www.familygenomics.systembiology.net/publications, retrieved on Jan. 14, 2014.
Bentley, "Whole-genome re-sequencing," Curr. Opin. Genet. Dev., 2006, pp. 545-552, vol. 16, No. 6.
Church, "Genomes for all," Scientific American, 2006, pp. 46-54, vol. 294, No. 1.
Dasgupta, "Brief Review of Regression-Based and Machine Learning Methods in Genetic Epidemiology: The Genetic Analysis Workshop 17 Experience," Genet. Epidemiol., 2011, pp. S5-11:1-13, 35(Suppl 1).
Kidd et al., "Mapping and sequencing of structural variation from eight human genomes," Nature, 2008, pp. 56-64, vol. 453, No. 7191.
Klein et al., "Complement Factor H Polymorphism in Age-Related Macular Degeneration," Science, 2005, pp. 385-389, vol. 308, No. 5720.
Liu et aL, "Comparison of Next-Generation Sequencing Systems," J. Biomed. Biotechnol., 2012:251364.
Nature Methods Editorial, "E pluribus unum," Nat. Methods, 2010, p. 331, vol. 7, No. 5.
Pettersson et al., "Generations of sequencing technologies," Genomics, 2009, pp. 105-111, vol. 93, No. 2.

(Continued)

*Primary Examiner* — Jerry Lin
(74) *Attorney, Agent, or Firm* — Polsinelli PC

(57) ABSTRACT

Ancestry has a significant impact on the major and minor alleles found in each nucleotide position within the genome. Due to mechanisms of inheritance, ancestral-specific information contained within the genome is conserved within members of an ancestry. For this reason, individuals within a specific ancestry are more likely to share alleles in their genomes with other members of the same ancestry. Functionally, the combination of alleles at all positions within a group of individuals defines that group as having a common ancestry. Moreover, the aggregation of differences between alleles at all positions distinguishes one ancestry from another. The genomic similarities and differences between ancestries provides a mechanism to generate reference genomes that are specific for each ancestry. Reference genomes that are specific to an ancestry can be used to increase the accuracy of whole genome sequencing, DNA-based diagnostics and therapeutic marker discovery and in a variety of real-world DNA-based applications. Provided herein is a method for determining a prognosis for a genetic disease or disorder comprising the step of comparing a DNA sequence of or derived from the whole genome of a patient with any one or combination of two or more ancestral-specific reference genomes of an ancestral-specific reference genome database described herein to determine the level of severity of the genetic disease or disorder.

20 Claims, 6 Drawing Sheets

(56) References Cited

OTHER PUBLICATIONS

Quail et al., "A tale of three next generation sequencing platforms: comparison of Ion torrent, pacific biosciences and Illumina MiSeq sequencers," BMC Genomics, 2012, 13:341.
Roach et al., "Analysis of Genetic Inheritance in a Family Quartet by Whole Genome Sequencing," Science, 2010, pp. 636-639, vol. 328, No. 5978.
Sanger et al., "A rapid method for determining sequences in DNA by primed synthesis with DNA polymerases," J. Mol. Biol., 1975, pp. 441-448, vol. 94, No. 3.
Scherer, "A short guide to the human genome," 1st Edition, Cold Spring Harbor Laboratory Press, Cold Spring Harbor, New York, 2008, p. 135.
Staden, "A strategy of DNA sequencing employing computer programs," Nucleic Acids Res., 1979, pp. 2601-2610, vol. 6, No. 7.
Wheeler, "The complete genome of an individual by massively parallel DNA sequencing," Nature, 2008, pp. 372-876, vol. 452, No. 7189.
Zhao et al., "Advances in Whole Genome Sequencing Technology," Curr. Pharm. Biotechnol., 2011, pp. 293-305, vol. 12, No. 2.

SEQUENCE LISTING

```
<160> NUMBER OF SEQ ID NOS: 3

<210> SEQ ID NO 1
<211> LENGTH: 8
<212> TYPE: DNA
<213> ORGANISM: Artificial Sequence
<220> FEATURE:
<223> OTHER INFORMATION: artificial sequence of exemplary reference
      genome

<400> SEQUENCE: 1 ttcacctc                                                                   8

<210> SEQ ID NO 2
<211> LENGTH: 8
<212> TYPE: DNA
<213> ORGANISM: Artificial Sequence
<220> FEATURE:
<223> OTHER INFORMATION: artificial sequence of exemplary ancestry
      specific reference genome

<400> SEQUENCE: 2 ttgacctc                                                                   8

<210> SEQ ID NO 3
<211> LENGTH: 8
<212> TYPE: DNA
<213> ORGANISM: Artificial Sequence
<220> FEATURE:
<223> OTHER INFORMATION: artificial sequence of exemplary patient DNA
      sequence

<400> SEQUENCE: 3 ttgaccac                                                                   8
```

ANCESTRAL-SPECIFIC REFERENCE GENOMES AND USES IN DETERMINING PROGNOSIS

1. CROSS-REFERENCE TO RELATED APPLICATIONS

This application is a divisional of U.S. Ser. No. 13/834,685, filed Mar. 15, 2013, and claims the benefit of U.S. Provisional Patent Application Ser. No. 61/694,155, filed on Aug. 28, 2012, each of which are incorporated herein by reference in their entirety.

2. FIELD OF THE INVENTION

Provided herein are ancestral-specific reference genome databases and methods of making and using such ancestral-specific reference genome databases.

The instant application contains a Sequence Listing which has been submitted in ASCII format via EFS-Web and is hereby incorporated by reference in its entirety. The Sequence Listing is being concurrently submitted via EFS-Web as an ASCII text file named 084453 540516 Sequence Listing.Txt, created Sep. 30, 2016.

3. BACKGROUND OF THE INVENTION

Much progress has been made in the development of high-throughput DNA sequencing technology in recent years (Pettersson E, Lundeberg J, Ahmadian A (February 2009). "Generations of sequencing technologies". Genomics 93 (2): 105-11. doi:10.1016/j.ygeno.2008.10.003. PMID 18992322; Staden, R (1979 Jun. 11). "A strategy of DNA sequencing employing computer programs". Nucleic Acids Research 6 (7): 2601-10. doi:10.1093/nar/6.7.2601. PMID 461197; Church G M (January 2006). "Genomes for all". Sci. Am. 294 (1): 46-54. doi:10.1038/scientificamerican0106-46. PMID 16468433). However, a comprehensive analysis of the entire genome is not currently commercially available or technologically possible. To date, whole genome sequencing is used only for research purposes (completegenomics.com/services/standard-sequencing/; illumina.com/services.ilmn), and a medically useful whole-genome-sequencing scale service simply does not exist.

While there are some reports of whole-genome-medical sequencing services, such services utilize information from the whole genome for only a few disease-associated single nucleotide polymorphisms (SNPs) in a limited number of genes (illumina.com/services.ilmn). This is in part because, although ancestral-specific mutations useful for medical applications of whole-genome sequencing have been generated in a variety of diseases (ncbi.nlm.nih.gov/omim), and Genome Wide Association Studies (GWAS) (Klein R J, Zeiss C, Chew E Y, Tsai J Y, Sackler R S, Haynes C, Henning A K, SanGiovanni J P, Mane S M, Mayne S T, Bracken M B, Ferris F L, Ott J, Barnstable C, Hoh J (April 2005). "Complement Factor H Polymorphism in Age-Related Macular Degeneration". Science 308 (5720): 385-9. doi:10.1126/science.1109557. PMC 1512523. PMID 15761122) has generated a partial list of ancestral SNPs for research purposes, a comprehensive list of whole genome-wide ancestral SNPs has not been generated to date. Without a comprehensive list of SNPs, the development of whole genome sequencing as a medical diagnostic tool may not be possible Progress in the area of whole genome sequencing as an approved diagnostic tool has been impeded largely because medical sequencing methods developed to date generate a large number of false positives and false negatives base calls inherent to the technology (Zhao J, Grant SF (February 2011). "Advances in Whole Genome Sequencing Technology". Curr Pharm Biotechnol 23(2) 293-305. PMID 21050163). There is an additional layer of misinformation generated in whole genome sequencing due to the current NIH-derived reference genome used as the standard template for sequencing (Scherer, Stewart (2008). A short guide to the human genome. CSHL Press. p. 135. ISBN 0-87969-791-1; Wheeler D A, Srinivasan M, Egholm M, Shen Y, Chen L, McGuire A, He W, Chen Y J, Makhijani V, Roth G T, Gomes X, Tartaro K, Niazi F, Turcotte C L, Irzyk G P, Lupski J R, Chinault C, Song X Z, Liu Y, Yuan Y, Nazareth L, Qin X, Muzny D M, Margulies M, Weinstock G M, Gibbs R A, Rothberg J M. (2008). "The complete genome of an individual by massively parallel DNA sequencing". Nature 452 (7189): 872-6; Bibcode 2008Natur.452 . . . 872W. doi:10.1038/nature06884. PMID 18421352). In particular, all of existing sequencing technologies utilize the same standard reference genome for the bioinformatic reconstruction/assembly of the whole genome from the small DNA fragments and sequenced during the process of obtaining a medically usable completed whole genome. The current standard reference genome, which was generated some years ago by the National Institutes of Health (NIH) as a model for genomic structure and sequence assembly, is based on a single whole genome sequence generated from the composite DNA obtained originally from five different individuals (Editorial (October 2010). "E pluribus unum". Nature Methods 331 (5): 331. doi:10.1038/nmeth0510-331). As such, it is neither statistically significant nor accurate when comparing individuals from different ancestral backgrounds and may not provide a statistically significant reference for interpreting genomic information.

Although some sequencing companies claim to have a very high accuracy rate for determining a whole genome sequence (Quail, Michael; Smith, Miriam E; Coupland, Paul; Otto, Thomas D; Harris, Simon R; Connor, Thomas R; Bertoni, Anna; Swerdlow, Harold P; Gu, Yong (1 Jan. 2012). "A tale of three next generation sequencing platforms: comparison of Ion torrent, pacific biosciences and illumina MiSeq sequencers". BMC Genomics 13 (1): 341. doi: 10.1186/1471-2164-13-341; Liu, Lin; Li, Yinhu; Li, Siliang; Hu, Ni; He, Yimin; Pong, Ray; Lin, Danni; Lu, Lihua; Law, Maggie (1 Jan. 2012). "Comparison of Next-Generation Sequencing Systems". Journal of Biomedicine and Biotechnology 2012: 1-11. doi:10.1155/2012/251364), the reality is, due to the large size of the genome (~3.2 billion base pairs coding for 20,000 to 25,000 distinct genes), even a small percentage of errors results in a large number of bases that are incorrectly called. A very low error rate is required for predictive medicine applications (Bentley D R (December 2006). "Whole-genome re-sequencing". Curr. Opin. Genet. Dev. 16 (6): 545-552. doi:10.1016/j.gde.2006.10.009. PMID 17055251; Genetest.org). Recently, bioinformatic tools have been developed that correct genomic sequence based on familial sequence information for an individual family (familygenomics.systemsbiology.net/publications). Including familial information from three closely related individuals can improve DNA sequence accuracy by 70%. Using information from four or more family members increases accuracy by 90% (Roach J C, Glussman G, Smit A F, Huff C D, Drmanac R, Jorde L B, Hood L, Galas D J (10 Apr. 2010) "Analysis of Genetic Inheritance in a Family Quartet by Whole Genome Sequencing". Science 328: 636-9 doi: 10.3410/f.2707961.2371060). However, such correction tools are time-consuming and add inefficiency and cost to the process of whole genome sequencing.

Accordingly, there is a need for the development of an ancestral-specific reference genome database that incorporates familial genome sequencing information to improve the accuracy of such ancestral-specific reference genomes. An ancestral-specific reference databases can, in turn, be used as tool, for example, for the diagnosis of a patent at risk for a genetic disease or disorder or for the prognosis of such a genetic disease or disorder.

4. SUMMARY OF THE INVENTION

Provided herein are methods for determining a prognosis for a genetic disease or disorder comprising the step of comparing a DNA sequence of or derived from the whole genome of a patient with any one or combination of two or more ancestral-specific reference genomes of an ancestral-specific reference genome database described herein to determine the level of severity of the genetic disease or disorder. In one embodiment, the disclosure provides a method of determining an individual's prognosis for a genetic disease or disorder with an ancestral-specific reference genome constructed by steps comprising: (a) obtaining a familial genome data set comprising DNA sequences from members of the individual's family; (b) comparing the DNA sequences within the familial genome data set to obtain a corrected familial genome data set; (c) preparing a first composite familial genome data set from the corrected familial genome data set; (d) repeating steps a-c for a second, third or more families to obtain a second, third or more composite familial genome data sets; (e) evaluating the first, second, third or more composite familial genome data sets for single nucleotide polymorphisms (SNPs) and/or haplotypes and assigning statistical significance to the SNPs and/or haplotypes; (f) grouping the first, second, third or more composite familial genome data sets based on single nucleotide polymorphisms (SNPs) and/or haplotypes that are statistically significant; (g) preparing the ancestral-specific reference genome by compiling the SNPs and/or haplotypes shared by a group of composite familial genome data sets with the same ancestry; and (h) comparing a DNA sequence of the individual's genome with the ancestral specific reference genome to determine the presence of a risk-modifying or disease-causing structural or functional variant within the ancestral specific reference genome that indicates the level of severity of the genetic disease or disorder.

In still another embodiment, the disclosure provides a method of determining a human's prognosis for a genetic disease or disorder with an ancestral-specific reference genome constructed by steps comprising: (a) obtaining a familial genome data set comprising DNA sequences from members of the human's family; (b) comparing the DNA sequences within the familial genome data set to obtain a corrected familial genome data set; (c) preparing a first composite familial genome sequence from the corrected familial genome data set; (d) repeating steps a-c for a second, third or more families to obtain a second, third or more composite familial genome data sets; (e) evaluating the first, second, third or more composite familial genome data sets for single nucleotide polymorphisms (SNPs) and/or haplotypes and assigning statistical significance to the SNPs and/or haplotypes; (f) grouping the first, second, third or more composite familial genome data sets based on single nucleotide polymorphisms (SNPs) and/or haplotypes that are statistically significant; (g) preparing the ancestral-specific reference genome by compiling the SNPs and/or haplotypes shared by a group of composite familial genome data sets with the same ancestry; and (h) comparing the DNA sequence of the human's genome with the ancestral-specific reference genome to determine the presence of a risk-modifying or disease-causing structural or functional variant within the ancestral specific reference genome that indicates the level of severity of the genetic disease or disorder.

Other embodiments are described in more detail below.

5. BRIEF DESCRIPTION OF DRAWINGS

Figure 5:
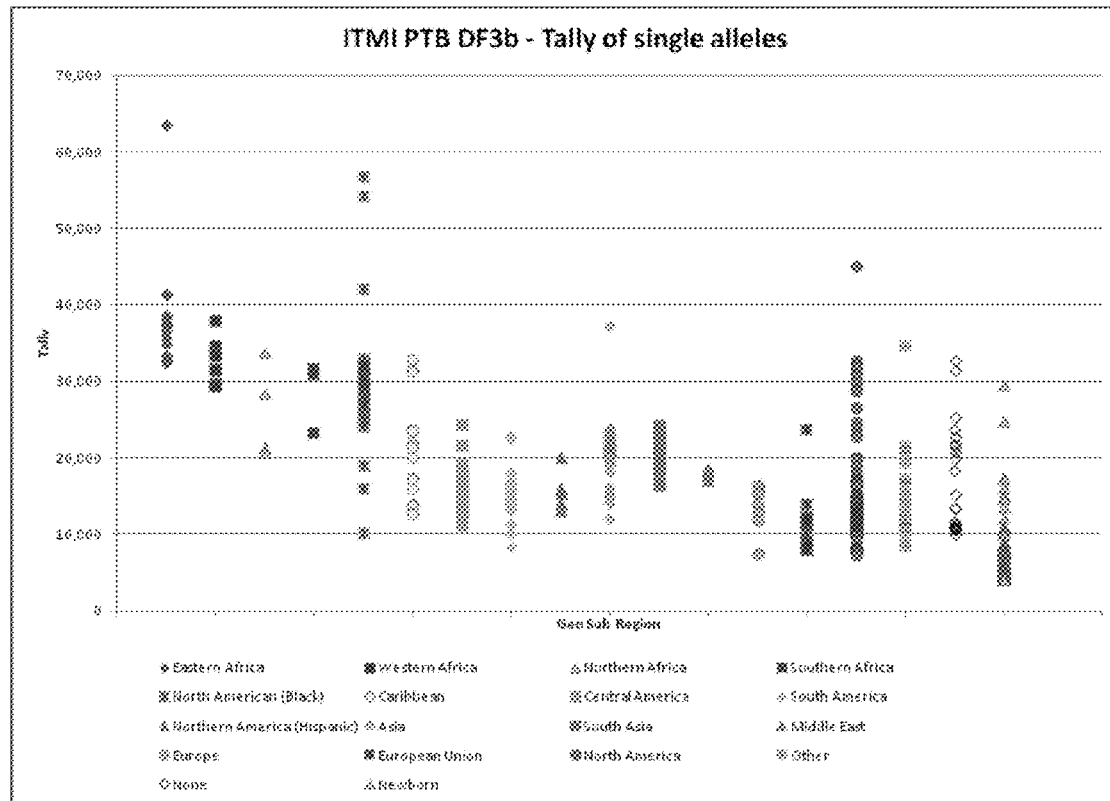

FIG. 5 shows the number of sequence variants by ancestry. Each column represents a different ethnicity. The number of variants is presented on the Y-axis. Individuals of African ancestry have the greatest number of variants when genomes are assembled to the standard NIH Reference Genome. By comparison, the North American and European Union genomes have the least variants, because they are derived from the same population used to generate the NIH Reference Genome.

Figure 6:
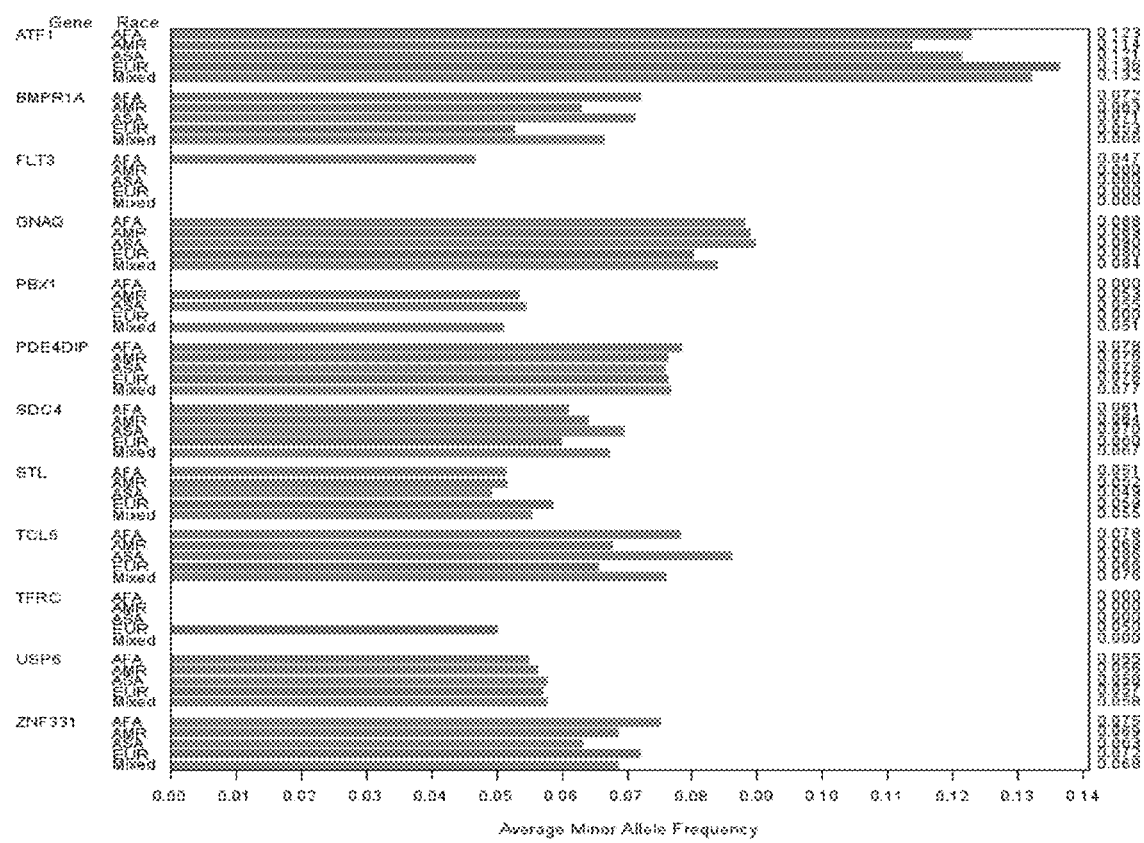

FIG. 6 identifies individual genes that show ancestral-specific differences. The FLT3 gene only has variants in the African population. The PBX1 gene has variants in the American and Asian populations, but not the African and European populations. The TFRC gene only contains variants in the European population. All other genes have a similar number of variants in all ancestries. Population-based differences in variant number demonstrates the variability between populations at the genetic level and thus the importance of considering ancestry when sequencing a member of an ancestral population.

6. DETAILED DESCRIPTION OF THE INVENTION

Provided herein are ancestral-specific reference genome databases and methods for their construction. In certain embodiments, the ancestral-specific reference genome database comprises a plurality of ancestral-specific reference genomes that are statistically significant, familial corrected, and phased referenced. It is believed that, on a whole genome scale, there are thousands of differences between ancestral groups that significantly affect how individuals within these different ancestral groups react to drug therapies and that, when disease occurs, can impact their prognosis, diagnosis and therapy (landesbioscience.com/curie/chapter/3119/). Based on the observation that the DNA of individuals from different ancestral groups contains ancestral-specific differences that are important to the interpretation of genomic sequencing information (Kidd, J M; et al. (2008). "Mapping and sequencing of structural variation from eight human genomes". *Nature* 453 (7191): 56-64. Bibcode 2008Natur.453 . . . 56K. doi:10.1038/nature06862. PMC 2424287. PMID 18451855), a number of ancestral-specific and statistically significant reference genomes were generated using a sufficient number of sequenced genomes (currently greater than 1,500 whole genomes and growing to >20,000). Such ancestral-specific genomes can be used, for example, to more accurately interpret genomic sequencing information for medically relevant diagnostic and prognostic purposes.

Terminology

The following illustrative explanations are provided to facilitate understanding of certain terms used frequently herein, particularly in the examples. The explanations are provided as a convenience and are not limitative of the invention.

Diagnostic Marker—A gene or DNA sequence with a known location and sequence on a chromosome that can be used to identify individuals within a species, specifically used in the diagnosis of genetic disease.

Whole Genome Sequencing—A laboratory process that determines the complete DNA sequence of an organism's genome at a single time.

Medical-Grade DNA Sequencing—A laboratory process that determines the complete DNA sequence of an organism's genome at a single time utilizing techniques that conform to standard quality laboratory methods outlined by the Clinical Laboratory Administration Act (CLIA), identifying all clinically relevant variants within a genome.

Haplotype—A group of alleles of different genes on a single chromosome that are linked closely enough to be inherited as a unit.

Ancestry—Persons initiating or comprising a line of descent.

Familial—Of or relating to a family, a group of people affiliated by consanguinity.

Database—A usually large collection of data organized especially for rapid search and retrieval (as by a computer).

Genome—One haploid set of chromosomes with the genes they contain; broadly: the genetic material of an organism.

Reference Genome—A digital nucleic acid sequence database, assembled by scientists as a representative example of a species' set of genes.

In silico—An expression used to mean "performed on computer or via computer simulation."

Single Nucleotide Polymorphisms (SNPs)—A DNA sequence variation occurring when a single nucleotide in the genome differs between members of a biological species or paired chromosomes in a human Variant—A single nucleotide polymorphism or rare genetic substitution event depending on the frequency in the population.

Figure 1:
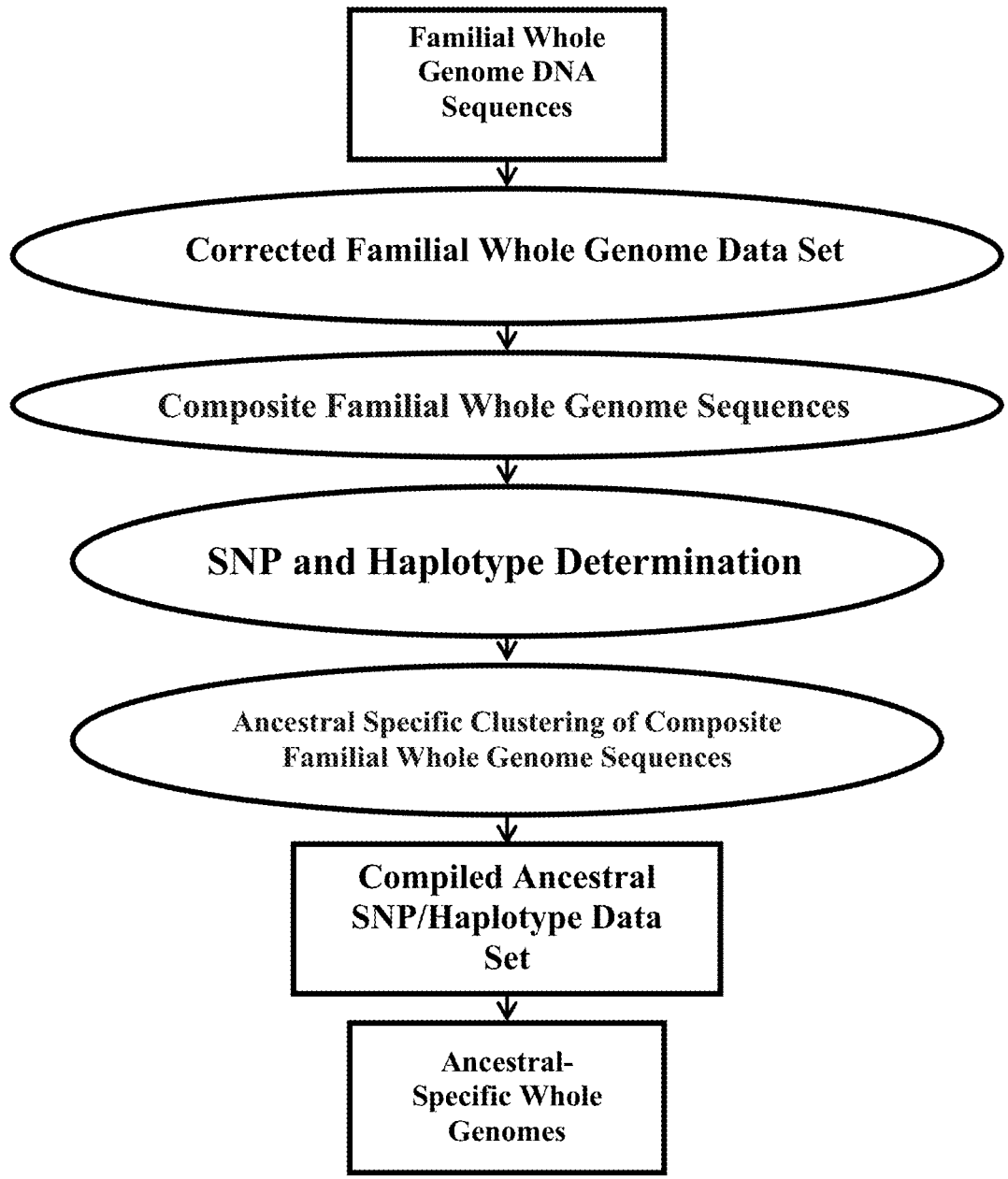
FIG. 1 represents an exemplary sequence of steps to generate ancestral-specific reference genomes from large amounts of whole genome DNA sequence information.

Minor Allele—An alternative form of the same gene or same genetic locus found in the minority of the population Major Allele—An alternative form of the same gene or same genetic locus found in the majority of the population 6.1 Methods for Generating Ancestral-Specific Reference Genomes The steps involved in generating the ancestral-specific reference genomes of such an ancestral-specific reference genome database are outlined in FIG. 1. The method described herein utilizes whole genome sequence data to generate familial whole genome data sets from a multiple individuals within a family. This sequence is corrected for content by comparing the genome sequence of related individuals with the family to obtain a corrected familial whole genome data set. These corrected sequences are then compiled into a composite familial whole genome sequence, in such a manner that ancestral-specific differences between the genomes are identifiable. Familial genomes can then be added to a composite familial whole genome sequence until the composite familial whole genome sequence reaches statistical significance. Upon reaching statistical significance, the composite familial whole genome sequence is evaluated for the presence of SNPs and haplotype. Statistical probabilities are assigned to each SNP and haplotype and the composite familial whole genome sequences are grouped according to statistically significant SNPs and/or haplotypes. The statistically significant SNPs and haploytpes can then be compiled into ancestral SNP and haplotype data sets. The ancestral-specific SNPs and/or haplotypes data sets can then be used to construct ancestral-specific reference genomes. A set of such ancestral-specific reference genomes describing ancestral and sub-ancestral groups can be utilized, for example, for medical diagnostics and research to target these groups, reducing the numbers of false positives and false negatives generated, and improving the efficiency of whole genome sequencing and enhancing performance of assays used in the development of personalized medicine applications.

Figure 3:
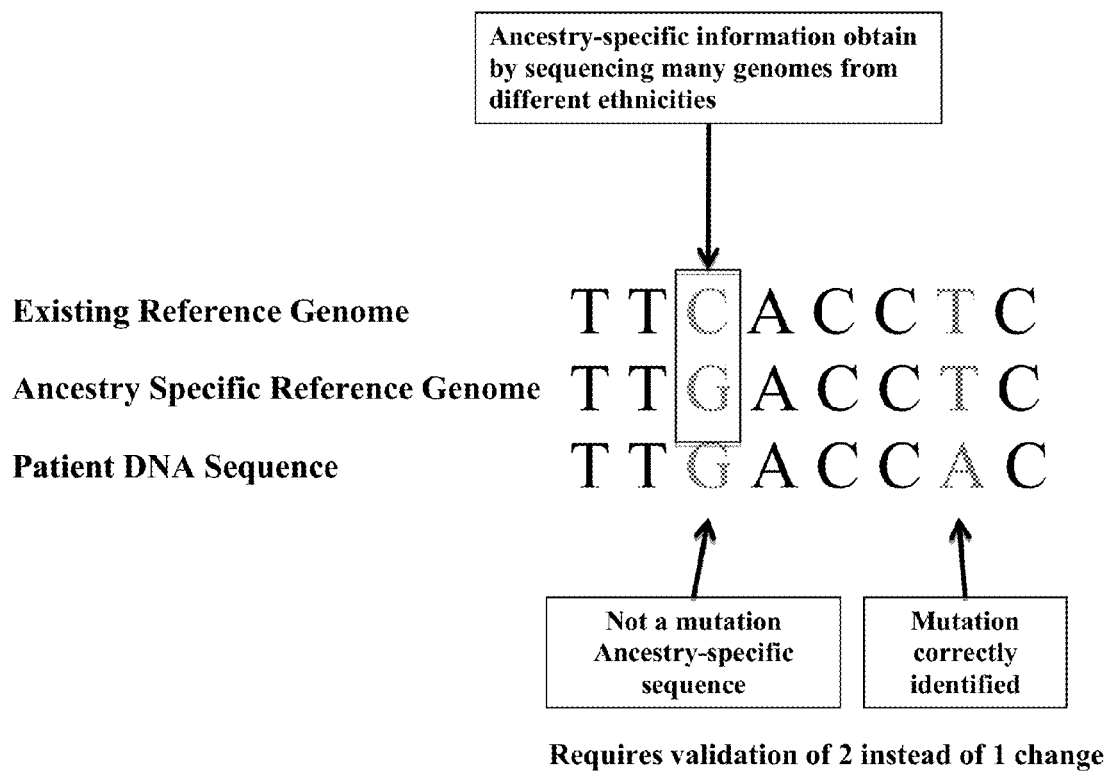
FIG. 3 represents an example of how ancestry specific reference genome information can be used to decrease the number of erroneous base calls generated by whole genome DNA sequencing and the impact on the need to validate such erroneous base calls by orthogonal sequencing technology.

The combination of familial-corrected sequences, ancestral-specific sequences, and statistical significance are all-critical to correcting the sequence to a sufficient level that the information can be used to evaluate a patient sample for mutations and disease-related SNPs. Without these corrections, the information obtained from DNA sequencing technologies generates so many false positives and false negatives that medical sequencing is currently outside of the realm of clinical utility as demonstrated in FIG. 3.

Figure 4:
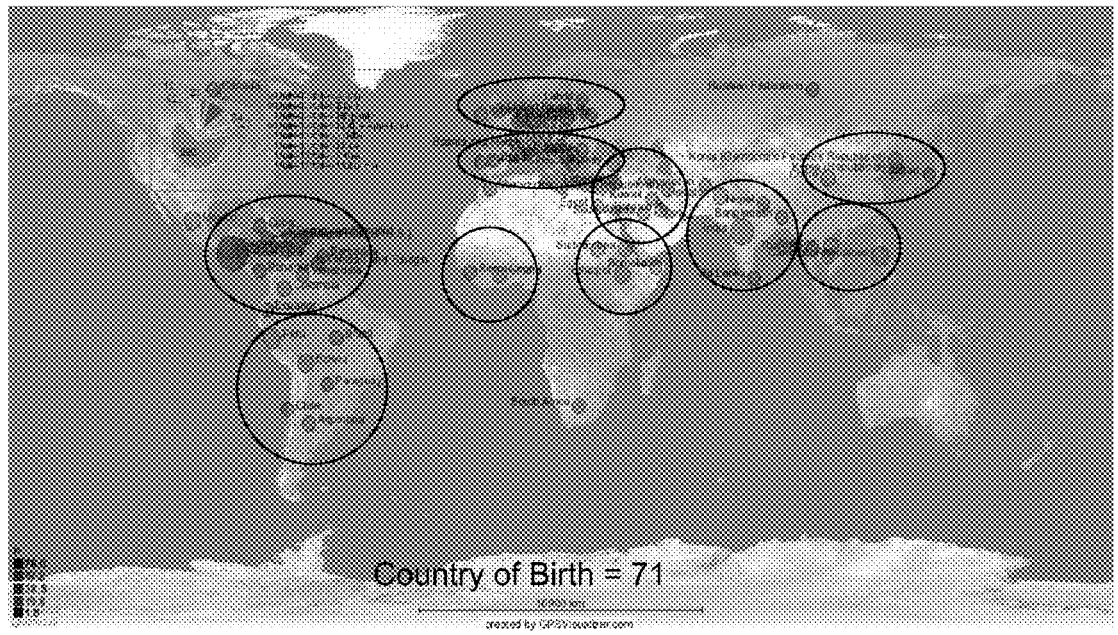
FIG. 4 shows a geographic distribution of countries of birth in Inova's whole genome sequence database. The ten large circles represent the ten ancestral genomes identified to date.

The geographic placement of the country of birth for individual genomes in ITMI's whole genome sequence database, currently comprising more than 2,000 whole genome sequences demonstrates that genomes are derived from 71 different countries. FIG. 4 shows how these countries of birth can be clustered into 10 ancestral genomes. The size of the circle is proportional to the number of genomes from that country. As more genomes are added to the database, the number of countries will increase, however, the greatest increase will be in the statistical significance achieved by each reference genome.

The number of variants found in each genome is a function of the difference between that genome and the NIH reference genome that is currently used to assemble and align genomes during the sequencing process. The larger the number of variants found in a genome, the greater the need for a reference genome that accounts for ancestry. FIG. 5 shows genomes clustered by ancestry in columns as a function of the number of variants on the Y-axis. The African genomes differ the most from the NIH reference genome which is represented by the North American genomes. As genomes are assembled, variation from the NIH reference genome is represented by an increase in the number of variants in a whole genome sequence. The consensus sequence from a group of genomes within an ancestry defines the basis of the reference genome that can be used for de novo assembly of genomes containing less variants and are thus more accurate representations of the individual genome.

At the genetic level ancestral variability is observed as differences in the number of variants in a gene. FIG. 6 shows the minor allele frequency for ten genes. Of the ten genes, there is ancestral variability within three. Using ancestral genomes would increase the ability to detect these difference at the genetic level and genomic level.

In one aspect, provided herein is a method for constructing an ancestral-specific reference genome databases comprising the steps of: a) obtaining a familial whole genome data set, comprising whole genome DNA sequences from three or more individuals of a first family; b) comparing the whole genome DNA sequences within the familial whole genome data set to obtain a corrected familial whole genome data set; c) preparing a first composite familial whole genome sequence from the corrected familial whole genome data set, wherein the first composite familial whole genome sequence comprises one or more single nucleotide polymorphisms (SNPs) and/or haplotypes; d) repeating steps a-c for second, third or more families to obtain second, third or more composite familial whole genome sequences; e) evaluating the first, second, third or more composite familial whole genome sequences for single nucleotide polymorphisms (SNPs) and haplotypes and assigning statistical probabilities to each of the SNPs and haplotypes; f) grouping the first, second, third or more composite familial whole genome sequences based on single nucleotide polymorphisms (SNPs) and/or haplotypes that are statistically significant; and g) preparing a plurality of ancestral-specific reference genome, each ancestral-specific reference genome based on the statistically significant SNPs and/or haplotypes shared by a group of composite familial whole genome sequences with the same ancestry.

In some embodiments, the method for constructing the ancestral-specific reference genome database comprises the step of obtaining a familial whole genome data set, comprising whole genome DNA sequences from three or more individuals of a first family.

As used herein, the term "family" refers to a group of individuals, related by blood, including individuals related to each other by the first degree (e.g., parents, full siblings, and children), second degree (grandparents, grandchildren, aunts, uncles, nephews, nieces and half-siblings), or third degree (first-cousins, great grandparents, and great grandchildren). In some embodiments, the familial whole genome data set comprises whole genome DNA sequences from four, five, six, seven, eight, nine, ten, eleven, twelve, thirteen, fourteen, fifteen, sixteen, seventeen, eighteen, nineteen, twenty or more individuals of a family. In some embodiments, the familial whole genome data set comprises whole genome DNA sequences from individuals of a family related to each other by ten degrees or less, by nine degrees or less, by eight degrees or less, by seven degrees, by six degrees or less, by five degrees, by four degrees or less, by three degrees or less, by two degrees or less, or by one degree.

Obtaining a familial whole genome data set, comprising whole genome DNA sequences from multiple individuals can be performed by any method known to those skilled in the art. In certain embodiments, the whole genome DNA sequences are obtained by performing a DNA sequencing reaction on whole genome DNA from three or more individuals from the same family. A DNA sequencing reaction can be performed using a commercially available sequencer such as those developed by Sanger (Sanger F, Coulson A R (May 1975). "A rapid method for determining sequences in DNA by primed synthesis with DNA polymerase". *J. Mol. Biol.* 94 (3): 441-8. doi:10.1016/0022-2836(75)90213-2. PMID 1100841), Life Technologies (invitrogen.com/site/us/en/home/Products-and-Services/Applications/Sequencing/Semiconductor-Sequencing/proton.html), Pacific Bio sciences (pacificbiosciences.com/), Illumina (illumina.com/) and Complete Genomics (completegenomics.com/) for example. In other embodiments, the whole genome DNA sequences are obtained from publicly available databases, including, but not limited to, databases developed by the International HapMap Project (hapmap.ncbi.nlm.nih.gov/); the National Center for Biotechnology Information, National Institutes of Health, Bethesda, Md. (NCBI) (ncbi.nlm.nih.gov/); and the European Molecular Biology Laboratory (EMBL) Nucleotide Sequence Database, Heidelberg, Germany (ebi.ac.uk/embl). In specific embodiments, the whole genome DNA sequences may, in part, be obtained from HapMap populations from the International HapMap Project.

In some embodiments, the method for constructing the ancestral-specific reference genome database comprises the step of comparing each whole genome DNA sequence within a familial whole genome data set, in whole or in part, against one another to obtain a corrected familial whole genome data set. In specific embodiments, the step of comparing whole genome DNA sequences within a familial whole genome data set comprises comparing every base position of a whole genome DNA sequence against other whole genome DNA sequences within the familial whole genome data set to determine differences in DNA sequences among the whole genome DNA sequences of the familial whole genome data set. In particular embodiments, a difference observed at a base position among the DNA sequences in a familial whole genome data set is validated using an orthogonal technology (e.g., two or more genome sequencing methods as described infra) to determine if the difference is due to an artifact of the platform used (e.g., an erroneous base call on the platform) or if the difference is a true nucleotide change. Differences in sequences due to errors are corrected to produce a corrected familial whole genome data set.

In some embodiments, the method for constructing the ancestral-specific reference genome database comprises the step of preparing a composite familial whole genome sequence, in whole or in part, from the corrected familial whole genome data set, wherein the composite familial whole genome sequence comprises one or more single nucleotide polymorphisms (SNPs) and/or haplotypes. Such composite familial whole genome sequences can be constructed, for example, using the information provided by the corrected familial whole genome data set, familial inheritance patterns and specifically developed analytic tools and algorithms.

In particular embodiments of the method, the steps of a) obtaining a familial whole genome data set, comprising whole genome DNA sequences, in whole or in part, from three or more individuals of a family; b) comparing the whole genome DNA sequences within the familial whole genome data set to obtain a corrected familial whole genome data set; c) preparing a composite familial whole genome sequence from the corrected familial whole genome data set, are repeated for a second, third or more families to obtain a second, third or more composite familial whole genome sequences. In certain embodiments of the method, the steps are repeated for 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 30 or more, 40 or more, 50 or more, 60 or more, 70 or more, 80 or more, 90 or more, or 100 or more families to obtain composite familial whole genome sequences for each of the families.

In particular embodiments, the method described herein comprises the step of evaluating the composite familial whole genome sequences, in whole or in part, for single nucleotide polymorphisms and/or haplotypes and assigning statistical probabilities to each of the SNPs and/or haplotypes. Any method known to those skilled in the art can be used to evaluate the presence of single nucleotide polymorphisms and haplotypes, including analytical tools that are available in the public domain (see, e.g., Haplo View, broadinstitute.org/scientific-community/science/programs/medical-and-population-genetics/haploview/haploview). Statistical significance of the SNPs and haplotypes are then determined for each SNPs and haplotype that are evaluated. A SNP is an "ancestral-specific SNP" if a particular allele of the SNP occurs at a frequency of greater than 99%, 95%, 90%, 85%, 80%, 75%, 70%, 65%, 60%, 55% or 50% as compared to the frequency at which it occurs in another distinct composite familial whole genome sequence. In certain embodiments, a SNP is an "ancestral-specific SNP" if it occurs at a frequency of greater than 99% as compared to the frequency at which it occurs in another distinct composite familial whole genome sequence. In certain embodiments, a SNP is an "ancestral-specific SNP" if it occurs at a frequency of greater than 95% as compared to the frequency at which it occurs in another distinct composite familial whole genome sequence. In certain embodiments, a SNP is an "ancestral-specific SNP" if it occurs at a frequency of greater than 90% as compared to the frequency at which it occurs in another distinct composite familial whole genome sequence. In certain embodiments, a SNP is an "ancestral-specific SNP" if it occurs at a frequency of greater than 85% as compared to the frequency at which it occurs in another distinct composite familial whole genome sequence. In certain embodiments, a SNP is an "ancestral-specific SNP" if it occurs at a frequency of greater than 80% as compared to the frequency at which it occurs in another distinct composite familial whole genome sequence. In certain embodiments, a SNP is an "ancestral-specific SNP" if it occurs at a frequency of greater than 75% as compared to the frequency at which it occurs in another distinct composite familial whole genome sequence. In certain embodiments, a SNP is an "ancestral-specific SNP" if it occurs at a frequency of greater than 70% as compared to the frequency at which it occurs in another distinct composite familial whole genome sequence. In certain embodiments, a SNP is an "ancestral-specific SNP" if it occurs at a frequency of greater than 65% as compared to the frequency at which it occurs in another distinct composite familial whole genome sequence. In certain embodiments, a SNP is an "ancestral-specific SNP" if it occurs at a frequency of greater than 60% as compared to the frequency at which it occurs in another distinct composite familial whole genome sequence. A haplotype is "ancestral-specific" if a particular haplotype occurs at a frequency of greater than 99%, 95%, 90%, 85%, 80%, 75%, 70%, 65%, 60%, 55% or 50% as compared to the frequency at which it occurs in another distinct composite familial whole genome sequence. In particular embodiments, these ancestral-specific SNPs/haplotypes are then used to generate ancestral-specific reference genomes of the ancestral-specific reference genome database.

In certain embodiments, an ancestral-specific reference genome of the ancestral-specific reference genome database comprises up to and including $1 \times 10^6$ or more SNPs. In certain embodiments, an ancestral-specific reference genome of the ancestral-specific reference genome database comprises up to and including $1.5 \times 10^6$ or more SNPs. In certain embodiments, an ancestral-specific reference genome of the ancestral-specific reference genome database comprises up to and including $2.0 \times 10^6$ or more SNPs. In certain embodiments, an ancestral-specific reference genome of the ancestral-specific reference genome database comprises up to and including $2.5 \times 10^6$ or more SNPs. In certain embodiments, an ancestral-specific reference genome of the ancestral-specific reference genome database comprises up to and including $3 \times 10^6$ or more SNPs. In certain embodiments, an ancestral-specific reference genome of the ancestral-specific reference genome database comprises up to and including $3.5 \times 10^6$ or more SNPs. In certain embodiments, an ancestral-specific reference genome of the ancestral-specific reference genome database comprises up to and including $4 \times 10^6$ or more SNPs. In certain embodiments, an ancestral-specific reference genome of the ancestral-specific reference genome database comprises up to and including $4.5 \times 10^6$ or more SNPs. In certain embodiments, an ancestral-specific reference genome of the ancestral-specific reference genome database comprises up to and including $5 \times 10^6$ or more SNPs. In certain embodiments, an ancestral-specific reference genome of the ancestral-specific reference genome database comprises up to and including $5.5 \times 10^6$ or more SNPs. In certain embodiments, an ancestral-specific reference genome of the ancestral-specific reference genome database comprises up to and including $6 \times 10^6$ or more SNPs. In certain embodiments, an ancestral-specific reference genome of the ancestral-specific reference genome database comprises up to and including $6.5 \times 10^6$ or more SNPs. In certain embodiments, an ancestral-specific reference genome of the ancestral-specific reference genome database comprises up to and including $7 \times 10^6$ or more SNPs. In certain embodiments, an ancestral-specific reference genome of the ancestral-specific reference genome database comprises up to and including $7.5 \times 10^6$ or more SNPs. In certain embodiments, an ancestral-specific reference genome of the ancestral-specific reference genome database comprises up to and including $8 \times 10^6$ or more SNPs. In certain embodiments, an ancestral-specific reference genome of the ancestral-specific reference genome database comprises up to and including $8.5 \times 10^6$ or more SNPs. In certain embodiments, an ancestral-specific reference genome of the ancestral-specific reference genome database comprises up to and including $9 \times 10^6$ or more SNPs. In certain embodiments, an ancestral-specific reference genome of the ancestral-specific reference genome database comprises up to and including $9.5 \times 10^6$ or more SNPs. In certain embodiments, an ancestral-specific reference genome of the ancestral-specific reference genome database comprises up to and including $1 \times 10^7$ or more SNPs. In certain embodiments, an ancestral-specific reference genome of the ancestral-specific reference genome database comprises up to and including $1.5 \times 10^7$ or more SNPs. In certain embodiments, an ancestral-specific reference genome of the ancestral-specific reference genome database comprises up to and including $2 \times 10^7$ or more SNPs. In certain embodiments, an ancestral-specific reference genome of the ancestral-specific reference genome database comprises up to and including $3 \times 10^7$ or more SNPs. In certain embodiments, an ancestral-specific reference genome of the ancestral-specific reference genome database comprises up to and including $4 \times 10^7$ or more SNPs. In certain embodiments, an ancestral-specific reference genome of the ancestral-specific reference genome database comprises up to and including $5 \times 10^7$ or more SNPs. The ancestral-specific SNPs identified using this method can be used to generate a composite ancestral-specific reference genome for each ancestral group analyzed.

The method described above can then be repeated and refined using subsets of individuals from each ancestral group. For example, the European ancestral-specific reference genome may be subdivided into an Eastern European-specific reference genome, Northern European specific reference genome, etc.

Figure 2:
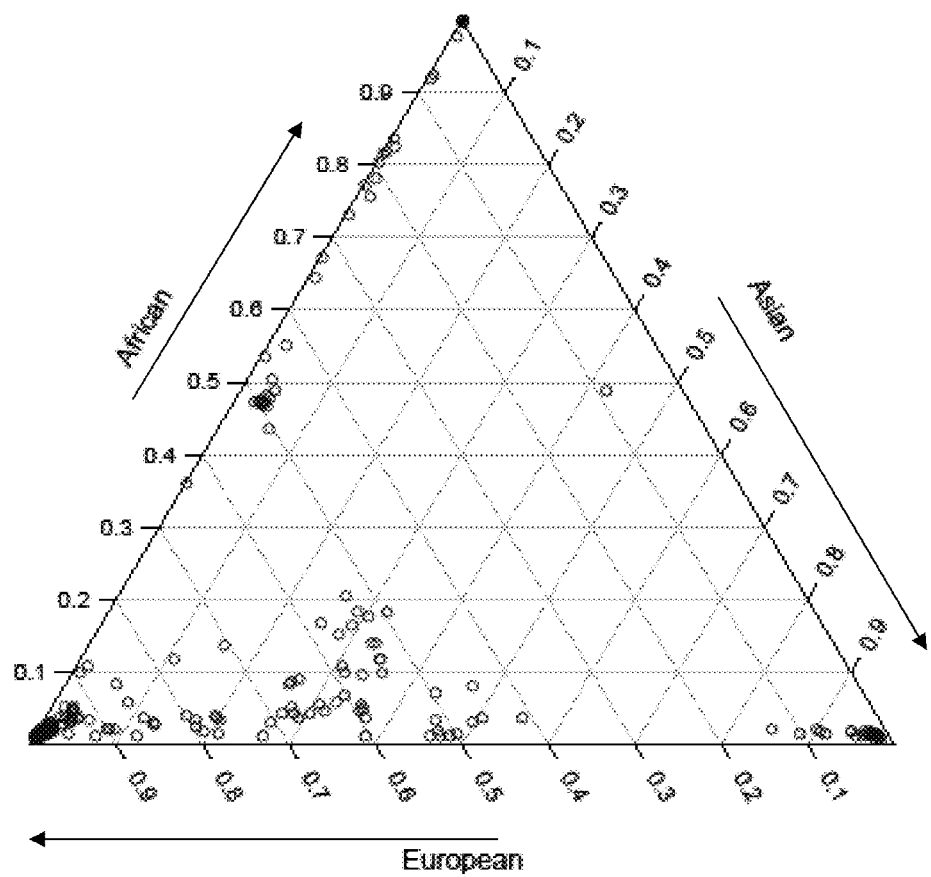
FIG. 2 shows a diagrammatic representation of how statistically significant, ancestral-specific SNPs can be used to construct ancestral-specific reference genomes.

The triangle shown in FIG. 2 depicts how this information is used to generate ancestral-specific reference genomes. Each of the corners of the triangle shown in FIG. 2 represents an ancestral group, i.e., European, African, or Asian. Markers that plot at the corners of the triangle represent ancestral-specific SNPs. For example, points that plot in the corner at the bottom right-hand sector of the triangle represent SNPs that are specific to individuals of European ancestry, because these variants occur in individuals of European ancestry, but not in individuals of African or Asian ancestries.

6.2 Uses of Ancestral-Specific Reference Genomes

The ancestral-specific reference genomes in whole or in part described herein have applications in the fields of analysis, DNA-based diagnostics, DNA sequencing, pharmaceutical drug development and clinical application of genomic information. These reference genomes make it possible to analyze whole genome or exome sequence data to generate more meaningful results by eliminating false positives and false negatives from the sequence data. The improved accuracy provided by ancestral-specific reference genomes permit the elimination of erroneous data. See FIG. 3.

The more accurate set of SNP and/or haplotype data generated from the results of this analysis may be placed in the context of other data, such as proteomic or pathway data, resulting in a more accurate interpretation of the impact of SNPs and/or haplotypes in the context of disease or for other applications as described in the examples listed below.

7. EXAMPLES 7.1 Enhanced Diagnostics

The field of DNA-based diagnostics relies on the ability to accurately identify DNA sequence, specifically in the nucleotide residues that result in disease-causing sequence variation. Accuracy of variant identification by sequence analysis is a major rate limiting step in the development of novel diagnostic markers and their use in testing the population. Variants identified utilizing enhanced reference genome translates into more accurate diagnostic markers and more accurate diagnostic tests. The utility of the reference genome for improving variant identification is independent of the technology used to generate variant information. By applying the information contained in the reference genome to the sequence technology utilized to generate the variant information, the interpretation of the variant information in enhanced. These markers can be used for prognostic or diagnostic testing for counseling of patients or as companion diagnostics for pharmaceutical compounds.

There are almost 1000 gene/SNP specific diagnostic tests available for medical diagnostics. This number is relatively small compared to the large number of potential disease-causing variants in the genome. These disease-causing variants occur in genetic disorders to include, but not limited to: Achromatopsia, Aicardi Syndrome, Albinism, Alexander Disease, Alpers' Disease, Alzheimer's Disease, Angelman Syndrome, Autism, Bardet-Biedl Syndrome, Barth Syndrome, Best's Disease, Bipolar Disorder, Bloom Syndrome, Canavan Syndrome, Cancer, including Breast Cancer, Prostate Cancer, Ovarian Cancer, and other forms of cancer, including cancers resultant from germ-line and somatic mutations, Carnitine Deficiencies, Cerebral Palsy, Coffin Lowry Syndrome, Heart Defects, Hip Dysplasia, Cooley's Anemia, Corneal Dystrophy, Cystic Fibrosis, Cystinosis Diabetes, Down Syndrome, Epidermolysis Bullosa, Familial Dysautonomia, Fibrodysplasia, Fragile X Syndrome, Deficiency Anemia, Galactosemia, Gaucher Disease, Gilbert's Syndrome, Glaucoma, Hemochromatosis, Hemoglobin C Disease, Hemophilia/Bleeding Disorders, Hirschsprung's Disease, Homocystinuria, Huntington's Disease, Hurler Syndrome, Klinefelter Syndrome, Macular Degeneration, Marshall Syndrome, Menkes Disease, Metabolic Disorders, Microphthalmus, Mitochondrial Disease, Mucolipidoses, Muscular Dystrophy, Neonatal Onset Multisystem Inflammatory Disease, Neural Tube Defects, Noonan Syndrome, Optic Atrophy, Osteogenesis Imperfecta, Peutz-Jeghers Syndrome, Phenylketonuria (PKU), Pseudoxanthoma Elasticum, Progeria, Scheie Syndrome, Schizophrenia, Sickle Cell Anemia, Skeletal Dysplasias, Spherocytosis, Spina Bifida, Spinocerebellar Ataxia, Stargardt Disease (Macular Degeneration), Stickler Syndrome, Toy-Sachs Disease, Thalassemia, Treacher Collins Syndrome, Tuberous Sclerosis, Turner's Syndrome, Urea Cycle Disorder, Usher's Syndrome or Werner Syndrome.

7.2 Ancestral-Specific Pharmaceutical Development

The development of pharmaceutical compounds is currently limited by the ability to identify groups within the general population that respond either favorably or unfavorably to a pharmaceutical compound. For example, it is possible to develop a pharmaceutical compound that has therapeutic efficacy in a sub-population, but the therapeutic effect may be obscured because that sub-population represents a minority in the general population. Similarly, it is possible to develop a pharmaceutical compound that has therapeutic efficacy in one sub-population, but has significant deleterious side effects in another sub-population. For this reason, it is advantageous to develop and evaluate pharmaceutical compounds at the sub-population level. The ancestral-specific nature of these reference genomes is critical to the development of ancestral-specific pharmaceutical compounds. As pharmaceutical companies are encouraged by the Food and Drug Administration (FDA) and economic factors to produce more narrowly focused therapeutics and diagnostics, these reference genomes provide the ability to determine in advance if a therapeutic is effective in a subgroup of the population.

7.3 Medical-Grade DNA Sequencing

Current DNA sequencing using the existing reference genomes is for research purposes only. Companies that claim to perform medical-grade DNA sequencing are utilizing research quality materials and methods in a CLIA environment to evaluate a limited number of variants in a small subset of the genes contained within the genome. The false positive and false negative errors introduced into the DNA sequence are the combined result of technological issues and the use of an inaccurate reference genome. Use of the ancestral reference genomes described herein provides a more accurate DNA sequencing method for the development of medical sequencing on a commercially feasible scale.

Currently, all DNA sequencing companies utilize the existing NIH reference genome; however, tailoring the reference to the particular genealogic background of the individual improves efficiency and accuracy of the final product. The current NIH reference genome is of limited utility because the sequence was generated from the DNA of only five individuals without regard to ancestry. Numerous versions of the NIH reference genome have been generated, correcting the reference sequence utilizing a variety of different datasets that also contain no ancestral information. The result is a reference genome that lacks statistical significance and haplotype information, and focuses only on major variants found in a single ancestry. Often, only minor variants are identified for nucleotide positions within the genome, or no call can be made based on the inability for current base-calling software to distinguish between two or more variants localized to the same nucleotide position. Ancestral-specific reference genomes that have been corrected with familial and haplotype information provide a mechanism for improving the quality of DNA sequencing to the point where it is medically useful.

The use of the ancestral reference genomes enhances the ability of clinicians to apply genomic information to their patients. If the genealogy of a patient is known or can be determined by the DNA sequence of the individual or family members, the clinician can use that information to determine which therapy may best suit the needs and the safety of the patient based on the availability of ancestral-specific therapeutic compounds.

7.4 Identification of Personal Attributes for Non-Medical Purposes

In another aspect, provided herein is an example of using ancestral-specific reference genomes, in whole or in part, for non-medical applications which utilize genomic sequence and SNP data to inform an individual about personal attributes such as ancestry, gender, compatibility between individuals based on actual or perceived physical, biological or psychological attributes, genetic compatibility or other information that can be obtained about an individual from their sequence information. This example specifically enables individuals to learn more about potential partners by comparing genomic information that has been enhanced for accuracy with ancestral-specific reference information. Other applications also exist. For example, individuals may use the reference genomes to compare the variant profile of their genes for physical ability, intellectual capacity or musical talent with a reference genome to improve the accuracy of comparisons.

In one embodiment, the method for identifying an individual attribute in an individual such as ancestry, personal compatibility, a physical attribute, a biological attribute, a psychological attribute or genetic compatibility, comprises the step of comparing a DNA sequence of an individual with any one or more of the ancestral-specific reference genomes of the ancestral-specific reference genome databases, wherein the one or more ancestral-specific reference genomes comprises one or more single nucleotide polymorphisms and/or haplotypes associated with a known individual attribute, and determining whether the DNA sequence of the individual also comprises the one or more single nucleotide polymorphisms and/or haplotypes associated with the known individual attribute.

7.5 Forensic Science Applications

In certain embodiments, the methods of using the ancestral-specific reference genome databases for forensic applications include, but are not limited to, paternity testing, improving identification of living or deceased individuals where conventional methods of identification fail, such as in a bomb blast, mass grave or natural disasters such as earthquakes and tidal waves. In the event that conventional methods of identification, such as fingerprint analysis, dental record review or DNA specific information that can be used to identify a person, comparison to reference genomes can provide information about a person's ancestry. For example, such an analysis could determine if a deceased individual is of Northern European versus Southern European descent, providing rescue groups or law enforcement or government agencies with information about a person's identity that they otherwise would not have.

7.6 Law Enforcement Applications

In other embodiments, the ancestral-specific reference genome databases and methods provided herein may be used in law-enforcement applications, such as the ancestral classification of an individual when a sample of their DNA is available that does not match an individual in law enforcement databases. Under such conditions, an unknown individual's DNA is used to determine the ancestry of the individual, making it possible to eliminate individuals outside of that ancestry as suspects and focusing the search for the guilty party to individuals from a specific ancestry. In another embodiment, ancestral reference genomes is used by government agencies such as the FBI or Department of Homeland Security to identify the ancestry of persons of interest such as terrorists, thus narrowing the search for persons of interest to a specific ancestry. In another embodiment, ancestral-specific reference genomes are applied to DNA-based information contained within FBI databases to improve the accuracy of identification of an individual. The improved accuracy resulting from the use of ancestral-specific reference genomes increases the statistical likelihood that the FBI has arrested the correct individual.

7.7 Reproduction Technologies

In another aspect, a method of using one or more ancestral-specific reference genome(s), in whole or in part, of an ancestral-specific reference genome database described herein for the selection of embryos, eggs or sperm for artificial reproduction. This includes the genetic evaluation of embryos, eggs and sperm for the detection of genetic disease, genomic disease, pharmacogenomic applications, determination of relatedness of individuals or the selection of physical attributes such as eye color or hair color or the identification of other attributes of interest to couples, physicians or scientists.

This also relates to paternity testing and to the typing of embryos for in vitro fertilization to minimize ancestral-related diseases such as in founder situations in inbred populations such as the Amish and Ashkenazi Jewish populations and to minimize the risk of genetic disease from reproduction by related individuals. In some embodiments, the method comprises the step of comparing a DNA sequence of an embryo, egg and/or sperm with any one or more of the ancestral-specific reference genomes of the ancestral-specific reference genome database of claim 1, wherein the one or more of the ancestral-specific reference genomes comprises one or more single nucleotide polymorphisms and/or haplotypes associated with a known genetic diseases, genomic attribute or physical characteristic, and determining whether the DNA sequence of the individual also comprises the one or more single nucleotide polymorphisms and/or haplotypes associated with the known genetic diseases, genomic attribute or physical characteristic. In some embodiments, the method comprises the step of comparing a DNA sequence of a sperm or egg of a first individual and the DNA sequence of a sperm or egg of a second individual with one or more ancestral-specific reference genomes, in whole or in part, of an ancestral-specific reference genome database described herein to determine the relatedness of the first individual and the second individual. The use of ancestral-specific reference genomes makes the analysis more accurate that current sequence analysis that utilizes the existing reference genome and thus increases the likelihood of the preferred outcome.

7.8 Non-Human Uses

In another aspect, provided herein is a method of using ancestral reference genomes, in whole or in part in other species for the selection of attributes. This includes, but is not limited to, the use of human and non-human reference genomes for identification of recombinant organisms that contain desired genotypes that may or may not confer a phenotype in the individual or lineage being evaluated. In one example, a "humanized mouse" animal model created in the laboratory to contain a part of or an entire human chromosome is evaluated for functional genes or DNA sequences contained in the hybrid. The advantage of utilizing ancestral-specific reference genomes is the improve accuracy of the DNA sequencing performed on these samples to ensure that the researcher is utilizing organisms that carry the variants necessary to achieve research goals.

In another embodiment, the reference genomes is used to improve the accuracy with which eggs, sperm or embryos are identified for the selective breeding of livestock, or the selection of microorganisms for research or industrial purposes, similar to its use in humans for reproductive technologies. In such instances, an organism-specific reference genome is created to facilitate the discrimination between different variants.

7.9 In Silico Genomics

In another aspect provided herein is a system comprising: (1) a central processing unit and (2) a memory coupled to the central processing unit, the memory storing one or more ancestral-specific reference genome databases provided herein. In certain embodiments, the memory further stores a nucleic acid comparison computer program wherein the nucleic acid sequencing computer program is capable of comparing the nucleic acid sequence of a sample nucleic acid with the plurality of ancestral-specific reference genomes of the one or more ancestral-specific reference genome databases to determine the presence of one or more ancestral-specific reference genome SNPs or haplotypes in the nucleic acid sequence of the sample nucleic acid sequence. In other embodiments, the system further comprises a user computer comprising an access software computer program that allows the access of the one or more ancestral-specific reference genome databases from the server computer. In yet other embodiments, the user computer further comprises a nucleic acid comparison computer program wherein the nucleic acid sequencing computer program is capable of comparing the nucleic acid sequence of a sample nucleic acid with the plurality of ancestral-specific reference genomes of the one or more ancestral-specific reference genome databases to determine the presence of one or more ancestral-specific reference genome SNPs or haplotypes in the nucleic acid sequence of the sample nucleic acid sequence.

The embodiments described herein are intended to be merely exemplary, and those skilled in the art will recognize, or be able to ascertain using no more than routine experimentation, numerous equivalents to the specific procedures described herein. All such equivalents are considered to be within the scope of the present invention and are covered by the following claims.

List of References

Pettersson E, Lundeberg J, Ahmadian A (February 2009). "Generations of sequencing technologies". Genomics 93 (2): 105-11. doi:10.1016/j.ygeno.2008.10.003. PMID 18992322.

Staden, R (1979 Jun. 11). "A strategy of DNA sequencing employing computer programs.". Nucleic Acids Research 6 (7): 2601-10. doi:10.1093/nar/6.7.2601. PMID 461197

Church G M (January 2006). "Genomes for all". Sci. Am. 294 (1): 46-54. doi:10.1038/scientificamerican0106-46. PMID 16468433 completegenomics.com/services/standard-sequencing illumina.com/services.ilmn ncbi.nlm.nih.gov/omim Klein R J, Zeiss C, Chew E Y, Tsai J Y, Sackler R S, Haynes C, Henning A K, SanGiovanni J P, Mane S M, Mayne S T, Bracken M B, Ferris F L, Ott J, Barnstable C, Hoh J (April 2005). "Complement Factor H Polymorphism in Age-Related Macular Degeneration". Science 308 (5720): 385-9. doi:10.1126/science.1109557. PMC 1512523. PMID 15761122

Zhao J, Grant S F (February 2011). "Advances in Whole Genome Sequencing Technology". Curr Pharm Biotechnol 23(2) 293-305. PMID 21050163

Scherer, Stewart (2008). A short guide to the human genome. CSHL Press. p. 135. ISBN 0-87969-791-1.

Wheeler D A, Srinivasan M, Egholm M, Shen Y, Chen L, McGuire A, He W, Chen Y J, Makhijani V, Roth G T, Gomes X, Tartaro K, Niazi F, Turcotte C L, Irzyk G P, Lupski J R, Chinault C, Song X Z, Liu Y, Yuan Y, Nazareth L, Qin X, Muzny D M, Margulies M, Weinstock G M, Gibbs R A, Rothberg J M. (2008). "The complete genome of an individual by massively parallel DNA sequencing". Nature 452 (7189): 872-6. Bibcode 2008Natur.452 . . . 872W. doi:10.1038/nature06884. PMID 18421352

Editorial (October 2010). "E pluribus unum". Nature Methods 331 (5): 331. doi:10.1038/nmeth0510-331

Quail, Michael; Smith, Miriam E; Coupland, Paul; Otto, Thomas D; Harris, Simon R; Connor, Thomas R; Bertoni, Anna; Swerdlow, Harold P; Gu, Yong (1 Jan. 2012). "A tale of three next generation sequencing platforms: comparison of Ion torrent, pacific biosciences and illumina MiSeq sequencers". BMC Genomics 13 (1): 341. doi: 10.1186/1471-2164-13-341

Liu, Lin; Li, Yinhu; Li, Siliang; Hu, Ni; He, Yimin; Pong, Ray; Lin, Danni; Lu, Lihua; Law, Maggie (1 Jan. 2012). "Comparison of Next-Generation Sequencing Systems". Journal of Biomedicine and Biotechnology 2012: 1-11. doi:10.1155/2012/251364

Bentley D R (December 2006). "Whole-genome re-sequencing". Curr. Opin. Genet. Dev. 16 (6): 545-552. doi: 10.1016/j.gde.2006.10.009. PMID 17055251; Genetest.org familygenomics.systemsbiology.net/publications Roach J C, GlussmanG, Smit A F, Huff C D, . . . Drmanac R, Jorde L B, Hood L, Galas D J (10 Apr. 2010) "Analysis of Genetic Inheritance in a Family Quartet by Whole Genome Sequencing". Science 328: 636-9 doi:10.3410/f.2707961.2371060 landesbioscience.com/curie/chapter/3119/

Kidd, J M; et al. (2008). "Mapping and sequencing of structural variation from eight human genomes". Nature 453 (7191): 56-64. Bibcode 2008Natur.453 . . . 56K. doi:10.1038/nature06862. PMC 2424287. PMID 18451855

Sanger F, Coulson A R (May 1975). "A rapid method for determining sequences in DNA by primed synthesis with DNA polymerase". J. Mol. Biol. 94 (3): 441-8. doi: 10.1016/0022-2836(75)90213-2. PMID 1100841 invitrogen.com/site/us/en/home/Products-and-Services/Applications/Sequencing/Semiconductor-Sequencing/proton.html
pacificbiosciences.com/
illumina.com/
completegenomics.com/
hapmap.ncbi.nlm.nih.gov/
ncbi.nlm.nih.gov/
ebi.ac.uk/embl/

All references (including patent applications, patents, and publications) cited herein are incorporated herein by reference in their entirety and for all purposes to the same extent as if each individual publication or patent or patent application was specifically and individually indicated to be incorporated by reference in its entirety for all purposes.

e) evaluating the first, second, third or more composite familial genome data sets for single nucleotide polymorphisms (SNPs) and/or haplotypes and assigning statistical significance to the SNPs and/or haplotypes;

f) grouping the first, second, third or more composite familial genome data sets based on single nucleotide polymorphisms (SNPs) and/or haplotypes that are statistically significant;

g) preparing the ancestral-specific reference genome by compiling the SNPs and/or haplotypes shared by a group of composite familial genome data sets with the same ancestry; and h) comparing a DNA sequence of the individual's genome with the ancestral specific reference genome to determine the presence of a risk-modifying or disease-

What is claimed is:

1. A method of determining an individual's prognosis for a genetic disease or disorder with an ancestral-specific reference genome constructed by steps comprising:

a) obtaining a familial genome data set comprising DNA sequences from members of the individual's family;

b) comparing the DNA sequences within the familial genome data set to obtain a corrected familial genome data set;

c) preparing a first composite familial genome data set from the corrected familial genome data set;

d) repeating steps a-c for a second, third or more families to obtain a second, third or more composite familial genome data sets;

causing structural or functional variant within the ancestral specific reference genome that indicates the level of severity of the genetic disease or disorder and making the individual's prognosis.

2. The method of claim 1, wherein the DNA sequence of the individual's genome is compared with the ancestral-specific reference genome with a nucleic acid comparison computer program.

3. The method of claim 1, further comprising the step of recording the ancestral-specific reference genome database onto a storage medium.

4. The method of claim 3, wherein the storage medium is a tangible storage medium or a cloud-based storage solution.

5. The method of claim 1, wherein the ancestral-specific reference genome is prepared by compiling the SNPs and/or haplotypes shared at a frequency of greater than 90%.

6. The method of claim 1, wherein the ancestral-specific reference genome is prepared by compiling the SNPs and/or haplotypes shared at a frequency of greater than 95%.

7. The method of claim 1, wherein the ancestral-specific reference genome is prepared by compiling the SNPs and/or haplotypes shared at a frequency of greater than 99%.

8. The method of claim 1, wherein the ancestral-specific reference genome has $1 \times 10^6$ or more SNPs.

9. The method of claim 1, wherein the ancestral-specific reference genome has $3 \times 10^6$ or more SNPs.

10. The method of claim 1, wherein the ancestral-specific reference genome has $6 \times 10^7$ or more SNPs.

11. The method of claim 1, wherein the members of the individual's family are first degree, second degree, or third degree blood relatives.

12. The method of claim 1, wherein the familial genome data set comprises genome DNA sequences from three or more members of the individual's family.

13. The method of claim 1, wherein the DNA sequence of the individual's genome is compared with the ancestral-specific reference genome to identify mutations that indicate the level of severity of the genetic disease or disorder.

14. The method of claim 1, wherein the individual is a human.

15. The method of claim 1, wherein the DNA sequences include whole genome DNA sequences and derivatives thereof.

16. The method of claim 1, wherein the DNA sequences include exome sequence data and derivatives thereof.

17. A method of determining a human's prognosis for a genetic disease or disorder with an ancestral-specific reference genome constructed by steps comprising:
   a) obtaining a familial genome data set comprising DNA sequences from members of the human's family;
   b) comparing the DNA sequences within the familial genome data set to obtain a corrected familial genome data set;
   c) preparing a first composite familial genome sequence from the corrected familial genome data set;
   d) repeating steps a-c for a second, third or more families to obtain a second, third or more composite familial genome data sets;
   e) evaluating the first, second, third or more composite familial genome data sets for single nucleotide polymorphisms (SNPs) and/or haplotypes and assigning statistical significance to the SNPs and/or haplotypes;
   f) grouping the first, second, third or more composite familial genome data sets based on single nucleotide polymorphisms (SNPs) and/or haplotypes that are statistically significant;
   g) preparing the ancestral-specific reference genome by compiling the SNPs and/or haplotypes shared by a group of composite familial genome data sets with the same ancestry; and
   h) comparing the DNA sequence of the human's genome with the ancestral-specific reference genome to determine the presence of a risk-modifying or disease-causing structural or functional variant within the ancestral specific reference genome that indicates the level of severity of the genetic disease or disorder and making the individual's prognosis.

18. The method of claim 17, wherein the DNA sequence of the human's genome is compared with the ancestral-specific reference genome with a nucleic acid comparison computer program.

19. The method of claim 17, further comprising the step of recording the ancestral-specific reference genome database onto a storage medium.

20. A method of determining a human's prognosis for a genetic disease or disorder with an ancestral-specific reference genome constructed by steps comprising:
   a) obtaining a familial whole genome data set comprising whole genome DNA sequences from three or more members of the human's family;
   b) comparing the whole genome DNA sequences within the familial whole genome data set to obtain a corrected familial whole genome data set;
   c) preparing a first composite familial whole genome data set from the corrected familial whole genome data set;
   d) repeating steps a-c for a second, third or more families to obtain a second, third or more composite familial whole genome data set;
   e) evaluating the first, second, third or more composite familial whole genome data sets for single nucleotide polymorphisms (SNPs) and/or haplotypes and assigning statistical significance to the SNPs and/or haplotypes;
   f) grouping the first, second, third or more composite familial whole genome data sets based on single nucleotide polymorphisms (SNPs) and/or haplotypes that are statistically significant;
   g) preparing the ancestral-specific reference genome by compiling the SNPs and/or haplotypes shared by a group of composite familial whole genome data sets with the same ancestry; and
   h) comparing the human's whole genome with the ancestral-specific reference genome to determine the presence of a risk-modifying or disease-causing structural or functional variant within the ancestral specific reference genome that indicates the level of severity of the genetic disease or disorder and making the individual's prognosis.

* * * * *